United States Patent
Chung et al.

(10) Patent No.: US 9,932,697 B2
(45) Date of Patent: Apr. 3, 2018

(54) STRUCTURE AND METHOD FOR CONNECTING FABRIC SENSOR AND DIGITAL YARN

(71) Applicant: KOREA INSTITUTE OF INDUSTRIAL TECHNOLOGY, Cheonan-si, Chungcheongnam-do (KR)

(72) Inventors: Gi Soo Chung, Cheonan-si (KR); Yoon Cheol Park, Seoul (KR)

(73) Assignee: Korean Institute of Industrial Technology, Chungcheongnam-Do (KR)

(*) Notice: Subject to any disclaimer, the term of this patent is extended or adjusted under 35 U.S.C. 154(b) by 182 days.

(21) Appl. No.: 14/902,131

(22) PCT Filed: Jul. 1, 2014

(86) PCT No.: PCT/KR2014/005829
§ 371 (c)(1),
(2) Date: Dec. 30, 2015

(87) PCT Pub. No.: WO2015/002424
PCT Pub. Date: Jan. 8, 2015

(65) Prior Publication Data
US 2016/0369441 A1    Dec. 22, 2016

(30) Foreign Application Priority Data
Jul. 2, 2013 (KR) .................... 10-2013-0077202

(51) Int. Cl.
*D05B 17/00*  (2006.01)
*A61B 5/0408*  (2006.01)
(Continued)

(52) U.S. Cl.
CPC .......... *D05B 17/00* (2013.01); *A61B 5/02055* (2013.01); *A61B 5/0408* (2013.01);
(Continued)

(58) Field of Classification Search
CPC ........ D05B 17/00; D05B 93/02; D05B 93/00; A61B 5/04085; A61B 5/02055; A61B 5/0006; A61B 5/6802
(Continued)

(56) References Cited

U.S. PATENT DOCUMENTS 6,668,380 B2 * 12/2003 Marmaropoulos .. A61N 1/0484
 2/69
7,395,106 B2 * 7/2008 Ryu .................... A61B 5/04085
 600/388
(Continued)

FOREIGN PATENT DOCUMENTS

CN    1817581 A    8/2006
CN    1882280 A    12/2006
(Continued)

OTHER PUBLICATIONS

International Search Report (in Korean with English Translation) for PCT/KR2014/005829, dated Oct. 23, 2014; ISA/KR.
(Continued)

*Primary Examiner* — Danny Worrell (57) ABSTRACT

Disclosed herein are structure and method for connecting a fabric sensor and a digital yarn. The structure includes a sheet-type member which is configured to be worn on a body of a wearer, a first fabric sensor which is provided on the sheet-type member and senses a biological signal, a digital yarn which is provided on the first fabric sensor and has a peeled portion that is electrically connected to the first fabric sensor, a sewing yarn which couples a portion of the digital yarn to the first fabric sensor by sewing, and a second fabric sensor which is coupled to the first fabric sensor and covers an upper portion of the peeled portion.

12 Claims, 6 Drawing Sheets

(51) Int. Cl.
*A61B 5/00* (2006.01)
*A61B 5/01* (2006.01)
*A61B 5/0205* (2006.01)
*A61B 5/021* (2006.01)
*A61B 5/024* (2006.01)
*A61B 5/08* (2006.01)
*A61B 5/11* (2006.01)
*A61B 5/145* (2006.01)

(52) U.S. Cl.
CPC .......... *A61B 5/6802* (2013.01); *A61B 5/6804* (2013.01); *A61B 5/01* (2013.01); *A61B 5/021* (2013.01); *A61B 5/0205* (2013.01); *A61B 5/02438* (2013.01); *A61B 5/02444* (2013.01); *A61B 5/0816* (2013.01); *A61B 5/11* (2013.01); *A61B 5/14532* (2013.01); *D05D 2303/40* (2013.01)

(58) Field of Classification Search
USPC .......................................... 112/154, 117, 157
See application file for complete search history.

(56) References Cited

U.S. PATENT DOCUMENTS

| | | | | |
|---|---|---|---|---|
| 7,783,334 | B2* | 8/2010 | Nam | A61B 5/04085 600/388 |
| 8,308,489 | B2* | 11/2012 | Lee | H01R 13/2407 2/69 |
| 8,909,318 | B2* | 12/2014 | Nordstrom | A61B 5/0006 600/388 |
| 9,282,893 | B2* | 3/2016 | Longinotti-Buitoni | A61B 5/02055 |
| 9,629,584 | B2* | 4/2017 | Macia Barber | A61B 5/04085 |
| 2006/0258205 | A1 | 11/2006 | Locher et al. | |
| 2007/0038057 | A1 | 2/2007 | Nam et al. | |
| 2010/0185076 | A1 | 7/2010 | Jeong et al. | |

FOREIGN PATENT DOCUMENTS

| | | |
|---|---|---|
| CN | 1976632 A | 6/2007 |
| JP | 2007023464 A | 2/2007 |
| KR | 1020070060971 A | 6/2007 |
| KR | 1020080114107 A | 12/2008 |
| KR | 1020090009645 A | 1/2009 |
| KR | 1020090110566 A | 10/2009 |

OTHER PUBLICATIONS

Written Opinion for PCT/KR2014/005829, dated Oct. 23, 2014; ISA/KR.

First Office Action dated May 4, 2017 from Chinese Patent Office for corresponding CN Serial No. 2014800383952 with included brief summarization of the Action from Chinese Associate (in English).

* cited by examiner

STRUCTURE AND METHOD FOR CONNECTING FABRIC SENSOR AND DIGITAL YARN

TECHNICAL FIELD

Exemplary embodiments of the present invention relate to structure and method for connecting a fabric sensor, which senses a biological signal of a wearer, with a digital yarn for transmission of the biological signal sensed by the fabric sensor.

BACKGROUND ART

In conventional methods for measuring biometric data such as the body temperature, pulse rate, electrocardiogram, and blood pressure of a patient, a process of measuring biometric data is performed in such a way that the patient or a medical personnel such as a doctor or a nurse brings a biometric data detecting sensor into contact with the body of the patient.

Examples of such measurement methods include a method of measuring the body temperature of the patient by putting a thermometer under the armpit of a patient for several minutes, and a method of measuring the pulse rate or blood pressure of the patient from the arm of the patient.

However, temporary biometric data which can be obtained by the above-mentioned measurement methods may not be enough to check conditions of a patient. For instance, despite the fact that the patient has felt symptoms, the symptoms may not appear when a doctor or nurse measures biometric data, and thus the patient may be diagnosed as normal.

In particular, symptoms of arrhythmia, heart rate abnormality, or the like may not always appear. In the case of a test for a short period of time, the mental state of the patient, the time zone of the test, etc. may affect the result of the test. Thus, the result of the diagnosis may not be accurate.

Recently, with the development of the information and communication technology, research on an e-health care technique capable of obtaining in real time biometric data anywhere and at any time and of using the obtained data has become appreciably more active.

Furthermore, such research leads to development of smart clothing, which can obtain biometric data about a wearer and transmit the obtained data to other devices, in various fields pertaining to, in particular, caring the aged people increasing in number as the population is aging, remotely treating or prescribing an emergency patient, checking the body stability of a soldier or high-risk worker, transmitting an alarm signal when a dangerous situation occurs, and so forth.

For example, smart clothing for measuring biological signals, in which a biological signal sensor forms a portion of the clothing and a first connector is coupled to the biological signal sensor, was proposed in Korean Patent Unexamined Publication No. 10-2009-0110566 (patent document 1). When a second connector provided on a display means or wireless transmission means is connected to the first connector, biological signals sensed by the biological signal sensor can be displayed on the display means or transmitted by the wireless transmission means.

In the case of patent document 1, the first connector having a snap button shape is required to transmit biological signals sensed by the biological signal sensor to the display means or the wireless transmission means. However, because the first connector must be made of metal, the cloth may be damaged when it is washed, and portions of the cloth that surrounds around the first connector may discolor because of corrosion of the first connector.

In addition, when a wearer wears the clothing, a portion of the first connector comes into direct contact with the body of the wearer, thus reducing wearing comfort, and giving a foreign body sensation when the wearer moves.

Furthermore, the biological signal sensor and the display means (or wireless transmission means) is connected to the first connector in a one-to-one manner. Therefore, it is impossible to use a plurality of biological signal sensors for measuring a variety of biological data such as a respiration rate, a pulse rate, a body temperature, etc. at the same time.

DISCLOSURE

Technical Problem

An object of the present invention is to provide structure and method for connecting a fabric sensor and a digital yarn which is capable of preventing cloth from being discolored or damaged even after it has been used for a long period of time or even when it is washed.

Another object of the present invention is to provide structure and method for connecting the fabric sensor and the digital yarn such that wearing comfort can be enhanced, and a wearer can move without discomfort.

Yet another object of the present invention is to provide structure and method for connecting a plurality of fabric sensors and a plurality of digital yarns such that a plurality of biological signal sensors can be used at the same time so as to obtain a variety of biometric data.

Technical Solution

In accordance with one aspect of the present invention, a structure for connecting a fabric sensor and a digital yarn includes: a sheet-type member configured to be worn on a body of a wearer; a first fabric sensor provided on the sheet-type member and sensing a biological signal; a digital yarn provided on the first fabric sensor with a peeled portion formed by peeling a portion of a sheath of the digital yarn, the peeled portion being electrically connected to the first fabric sensor; a sewing yarn coupling a portion of the digital yarn to the first fabric sensor by sewing; and a second fabric sensor coupled to the first fabric sensor and covering an upper portion of the peeled portion.

In the structure for connecting a fabric sensor and a digital yarn in accordance with another aspect of the present invention, the peeled portion may be formed on an upper portion of the digital yarn, and the second fabric sensor may be electrically connected to the peeled portion.

In the structure for connecting a fabric sensor and a digital yarn in accordance with another aspect of the present invention, the second fabric sensor may be adhered to the first fabric sensor by a conductive adhesive.

In the structure for connecting a fabric sensor and a digital yarn in accordance with another aspect of the present invention, the second fabric sensor may be sewn to the first fabric sensor along a perimeter of the second fabric sensor.

In the structure for connecting a fabric sensor and a digital yarn in accordance with another aspect of the present invention, a third fabric sensor may be coupled to the second fabric sensor, and an elastic member may be interposed between the second fabric sensor and the third fabric sensor.

In the structure for connecting a fabric sensor and a digital yarn in accordance with another aspect of the present invention, the digital yarn may be disposed on the first fabric sensor in a zigzag form, and the sewing yarn may be sewn to a vertex of the zigzag-formed digital yarn.

A method for connecting a fabric sensor and a digital yarn in accordance with an aspect of the present invention include: (a) coupling a first fabric sensor to a sheet-type member configured to be worn on a body of a wearer; (b) coupling a digital yarn to the first fabric sensor; and (c) peeling a portion of a sheath of the digital yarn and electrically connecting the digital yarn to the first fabric sensor, wherein (b) coupling comprises sewing the digital yarn to the first fabric sensor using a sewing yarn crossing over a portion of the digital yarn, and the method further includes (d) coupling a second fabric sensor to the first fabric sensor and covering an upper portion of the peeled portion of the digital yarn with the second fabric sensor.

In the method for connecting a fabric sensor and a digital yarn in accordance with another aspect of the present invention, (b) coupling may include disposing the digital yarn on the first fabric sensor in a zigzag form, and sewing the sewing yarn to a vertex of the zigzag-formed digital yarn.

In the method for connecting a fabric sensor and a digital yarn in accordance with another aspect of the present invention, the peeled portion may be formed by peeling an upper portion of the sheath of the digital yarn, and the second fabric sensor may be electrically connected to the peeled portion.

In the method for connecting a fabric sensor and a digital yarn in accordance with another aspect of the present invention, (d) coupling may include adhering the second fabric sensor to the first fabric sensor using a conductive adhesive.

In the method for connecting a fabric sensor and a digital yarn in accordance with another aspect of the present invention, (d) coupling may include sewing the second fabric sensor to the first fabric sensor along a perimeter of the second fabric sensor.

The method for connecting a fabric sensor and a digital yarn in accordance with another aspect of the present invention may further include (e) coupling a third fabric sensor to the second fabric sensor with an elastic member interposed between the second fabric sensor and the third fabric sensor.

Advantageous Effects

In structure and method for connecting a fabric sensor and a digital yarn according to an embodiment of the present invention, a biological signal sensed by a fabric sensor is transmitted through a digital yarn that is integrally formed with a sheet-type member such as clothes or sewn to one surface of the sheet-type member. Therefore, wearing comfort can be improved, and a wearer can move without discomfort.

Furthermore, because the digital yarn is used to transmit a biological signal sensed by the fabric sensor, cloth can be prevented from being discolored or damaged even after it has been used for a long period of time or even when it is washed, unlike the conventional technique using the metal connector.

Moreover, in the case where a plurality of biological signal sensors to which respective digital yarns are connected are used, a variety of biometric data can be obtained at the same time by the plurality of biological signal sensors.

MODE FOR INVENTION

Hereinafter, exemplary embodiments of structure and method for connecting a fabric sensor and a digital yarn according to the present invention will be described with reference to the attached drawings. For reference, the size of each element, the thickness of lines indicating the element, etc. may be exaggeratedly expressed in the drawings for the sake of understanding the present invention.

The terms and words used for elements in the description of the present invention are determined based on the functions of the elements in the present invention. The terms and words may be changed depending on the intention or custom of users or operators, so that they must be defined based on the whole content of the present specification.

The following embodiments are disclosed only for illustrative purposes and should not be construed as limiting the present invention. The present invention is intended to cover not only the exemplary embodiments, but also various alternatives, modifications, equivalents and other embodiments that may be included within the spirit and scope of the present invention as defined by the appended claims.

The term "digital yarn" used in this specification refers to a yarn which allows transfer of electrons for transmission of information and can be used in weaving or knitting. In the present invention, the digital yarn has the same function as that of a circuit wire connecting electric or electronic modules on a circuit board of an electronic product and thus makes data transmission possible. In other words, the digital yarn connects a sensor for sensing biometric data to various devices (for example, a display, a communication device, or a storage device) and thus enables transmission of information data therebetween.

Embodiments

Figure 1:
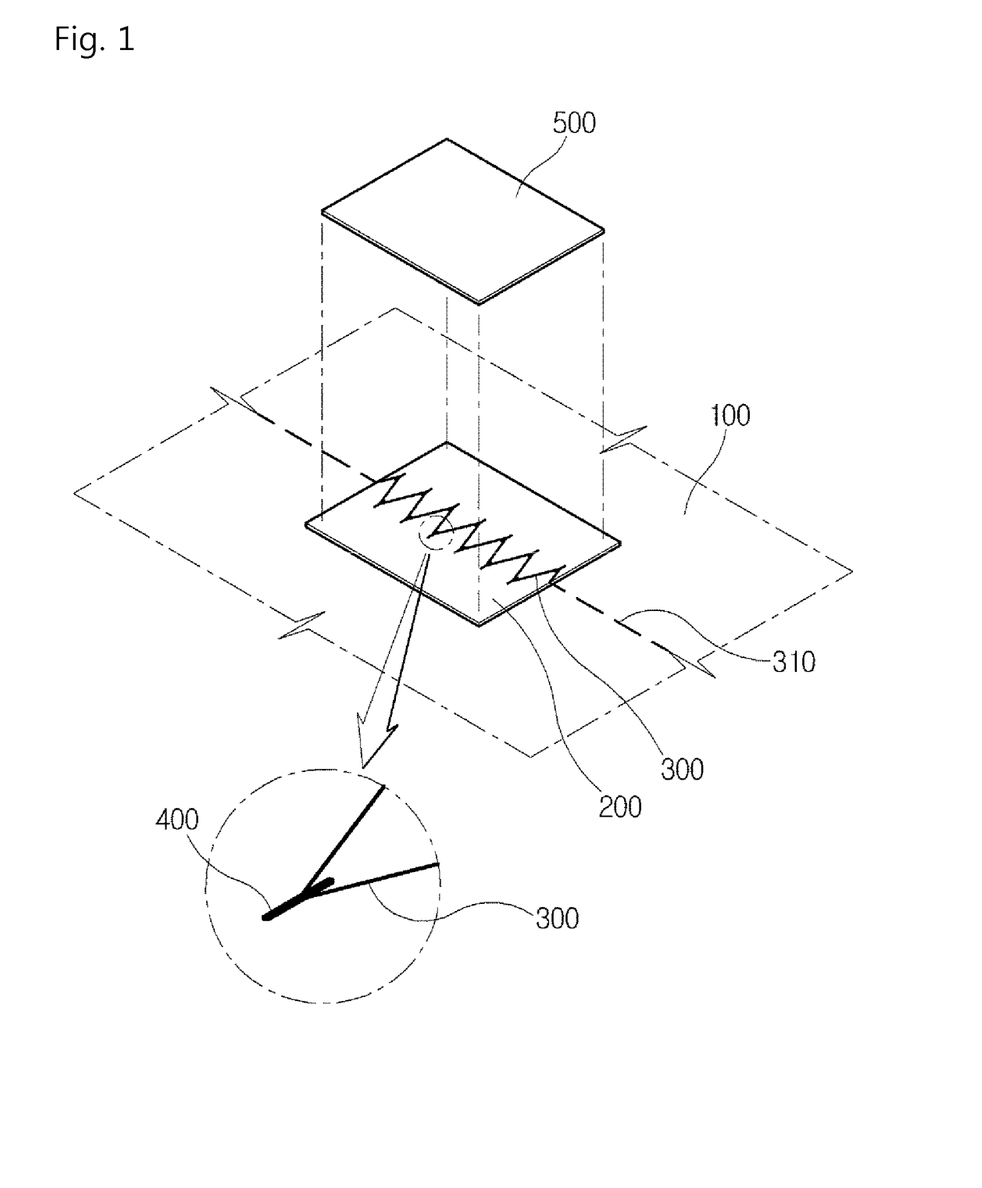
FIG. 1 is an exploded perspective view illustrating a structure for connecting a fabric sensor and a digital yarn according to an embodiment of the present invention.

FIG. 1 is an exploded perspective view illustrating a structure for connecting a fabric sensor and a digital yarn according to an embodiment of the present invention.

As shown in FIG. 1, the structure for connecting the fabric sensor and the digital yarn according to the present embodiment includes a sheet-type member 100 which is worn on the body of a wearer, a first fabric sensor 200 which is provided on the sheet-type member 100, a digital yarn 300 which is connected to the first fabric sensor 200, and a sewing yarn 400 which fastens the digital yarn 300 to the first fabric sensor 200.

The sheet-type member 100 is worn on the body of the wearer and has a surface to which the fabric sensor is coupled. The sheet-type member 100 may be formed in a form of an elastic band or clothes such as upper clothes or lower clothes. Preferably, the sheet-type member 100 is formed by weaving material such as natural or synthetic fibers.

The first fabric sensor 200 is embodied in a fabric form and is preferably configured such that it can come into close contact with the body of the wearer so as to comparatively precisely sense biometric data even when the body of the wearer moves. Furthermore, for the sake of convenience, the first fabric sensor 200 is preferably made of elastic fabric.

The first fabric sensor 200 senses at least one piece of biometric data such as a body temperature, a pulse rate, a respiration rate, an electrocardiogram, a blood pressure, a blood sugar, or momentum. When the sheet-type member 100 is formed by weaving, the first fabric sensor 200 may be integrally formed with the sheet-type member 100 so that the first fabric sensor 200 forms a portion of the sheet-type member 100. Alternatively, as shown in FIG. 1, the first fabric sensor 200 having a predetermined area may be separately fabricated from the sheet-type member 100 and then coupled to the sheet-type member 100.

In this case, the first fabric sensor 200 may be attached to the sheet-type member 100 by a conductive adhesive. In another method, the first fabric sensor 200 may be fastened to the sheet-type member 100 by sewing, backstitching, embroidering, etc. in such a way that a sewing line is formed along the perimeter of the first fabric sensor 200. As a further alternative, the perimeter of the first fabric sensor 200 may be fused to the sheet-type member 100.

Preferably, the first fabric sensor 200 is disposed such that it comes into direct contact with the body of the wearer or faces the body when the wearer wears the sheet-type member 100. That is, when the wearer wears the sheet-type member 100, the first fabric sensor 200 is disposed inside the sheet-type member 100.

The location at which the first fabric sensor 200 is disposed on the sheet-type member 100 can be appropriately selected depending on the kind of body data to be measured by the first fabric sensor 200. For instance, when the first fabric sensor 200 is intended to be used for an electrocardiogram, it is preferable that if the sheet-type member 100 is clothes, the first fabric sensor 200 be disposed such that when the wearer wears the clothes, the first fabric sensor 200 is located adjacent to the heart of the wearer. In the case where the sheet-type member 100 is an elastic band, the wearer wears the elastic band around his/her chest such that the first fabric sensor 200 is located around his/her heart.

The digital yarn 300 is connected to a portion of the first fabric sensor 200. The digital yarn 300 may extend traversing the first fabric sensor 200. Alternatively, one end of the digital yarn 300 may be connected to the first fabric sensor 200. The digital yarn 300 functions as a circuit line which transmits a biological signal sensed by the first fabric sensor 200 to a separate display (not shown) or a wireless transmitter (not shown).

For example, a connector (not shown) having a plurality of connection pins may be provided on a portion (e.g., in the case of clothes, a pocket provided on a lower portion of a front side of the clothes) of the sheet-type member 100. Multiple pieces of biometric data may be transmitted at the same time to the connector through a plurality of digital yarns 300 which are connected to a plurality of respective fabric sensors.

When the display is connected to the connector, multiple pieces of biometric data transmitted from a plurality of fabric sensors can be directly displayed. A wireless transmitter may be connected to the connector. Biometric data transferred from the fabric sensors is wirelessly transmitted to and stored in an external data processing unit (not shown) such as a PC or a cellular phone, and the biometric data measured by the various kinds of fabric sensors is displayed on a display of the data processing unit.

The digital yarn 300 extends from the first fabric sensor 200 to a device such as a display, a wireless transmitter, or a connector in such a way that the digital yarn 300 is sewn to the sheet-type member 100. Here, when the sheet-type member 100 is woven, fibers forming the sheet-type member 100 and the digital yarn 300 may be woven together so that the digital yarn 300 can form a portion of the sheet-type member 100. Alternatively, the digital yarn 300 may be separately sewn to the sheet-type member 100 and thus form a sewing line.

With regard to the connection between the first fabric sensor 200 and the digital yarn 300, a fusing method or a method using a conductive adhesive may be used as another example. However, in the case of the fusion method, the production cost is increased, and there is the probability of a reduction in reliability of measurement values because of thermal deformation of the internal structure of the first fabric sensor 200 or the digital yarn 300. In the case of the method using a conductive adhesive, reliable connection between the first fabric sensor 200 and the digital yarn 300 cannot be ensured, in other words, there is the probability of an adhesive layer forming part being detached due to creases formed on the sheet-type member 100, e.g., when the sheet-type member 100 is washed or worn on the body of the wearer. In addition, because it takes a long time to harden the adhesive, the method using a conductive adhesive is not adapted to mass production.

The digital yarn 300 is disposed on the first fabric sensor 200 in a zigzag form and is fastened to the first fabric sensor 200 by the sewing yarn 400 which is sewn to the first fabric sensor 200 across the vertices of the zigzag-formed digital yarn 300. For example, as shown in FIG. 1, the digital yarn 300 may be disposed on the first fabric sensor 200 in a longitudinally zigzag form. The sewing yarn 400 may be sewn to the first fabric sensor 200 at the vertices of the zigzag-formed the digital yarn 300. The sewing yarn 400, sewn to the first fabric sensor 200, wraps around the outer circumferential surface of the digital yarn 300 with respect to the vertical direction.

That is, a plurality of portions of the digital yarn 300 that are spaced apart from each other with respect to the longitudinal direction are fastened in a zigzag manner to the first fabric sensor 200 by the sewing yarn 400. Preferably, a sewing machine is used to sew the digital yarn 300 to the first fabric sensor 200 using the sewing yarn 400. As needed, any one of various methods, for example, backstitching, may be selected as a method of sewing the digital yarn 300 to the first fabric sensor 200 using the sewing yarn 400. With regard to the sewing yarn 400 by which the vertices of the zigzag-formed digital yarn 300 are sewn to the first fabric sensor, a plurality of sewing yarns 400 may be used and separately finished at the respective vertices of the zigzag-formed digital yarn 300 or, alternatively, a single sewing yarn 400 may be used for the vertices of the zigzag-formed digital yarn 300 and finished at one time.

The sewing yarn 400 may be made of any one of synthetic fibers or natural fibers, such as cotton, silk, or hemp. Furthermore, the sewing yarn 400 may have a single yarn structure or a multi-plied yarn structure formed by twisting a plurality of single yarns together. Although the single digital yarn 300 is illustrated as being connected to the first fabric sensor 200 in the embodiment of FIG. 1, a plurality of digital yarns may be connected to the first fabric sensor 200, as needed. Furthermore, a plurality of digital yarns 300 may only extend over the first fabric sensor 200 without making electric connection with the first fabric sensor 200.

Figure 3:
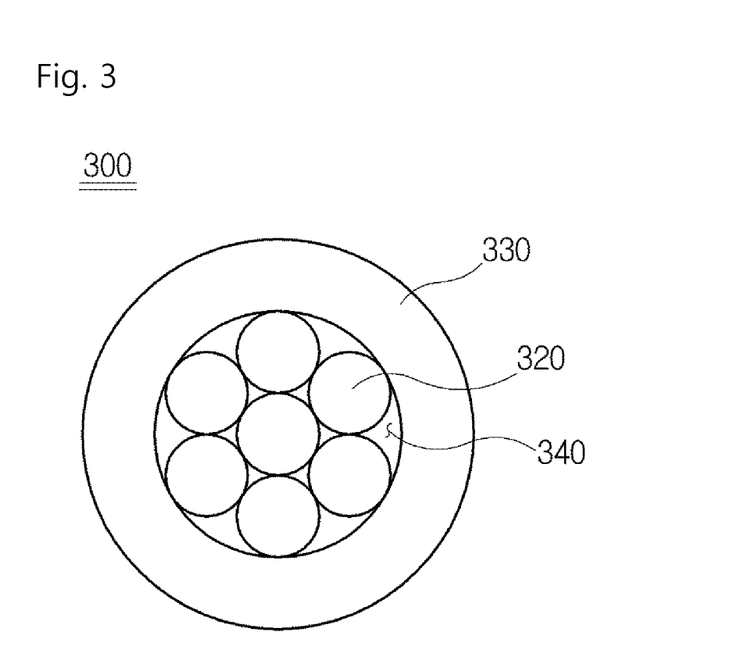
FIG. 3 is a sectional view showing a digital yarn according to an embodiment of the present invention.

For electrical connection between the first fabric sensor 200 and the digital yarn 300, a portion of the digital yarn 300 is peeled. In detail, as shown in FIG. 3, the digital yarn 300 includes a plurality of cores 320 which are made of metal, and a sheath 330 which is made of insulating material and encloses the cores 320. Therefore, to transmit through the digital yarn 300 an electrical signal sensed by the first fabric sensor 200, a portion of the sheath 330 of the digital yarn 300 must be removed so that the first fabric sensor 200 and the cores 320 of the digital yarn 300 can be electrically connected to each other.

A peeled portion (formed by peeling a portion of the sheath of the digital yarn) of the digital yarn 300 can be formed on any portion of the digital yarn 300 that is disposed on the first fabric sensor 200, so long as the first fabric sensor 200 can be elastically connected to the cores 320 of the digital yarn 300 through the peeled portion.

To reliably maintain the electrical connection between the peeled portion and the first fabric sensor 200, it is preferable that a plurality of peeled portions be formed by peeling several portions of the sheath 300 of the digital yarn 300 sewn to the first fabric sensor in a linear or zigzag form. Furthermore, it is preferable that at least one peeled portion be formed around the vertices of the zigzag-formed digital yarn 300 that are compressed by the sewing yarn 400.

A second fabric sensor 500 is coupled on the first fabric sensor 200 to which the digital yarn 300 is connected. The second fabric sensor 500 functions as a cover which covers and protects the junction between the digital yarn 300 and the first fabric sensor 200 so that it can be prevented from being exposed to the outside. Furthermore, the second fabric sensor 500 is electrically connected to the peeled portion of the digital yarn 300 so that an electrical signal sensed by the second fabric sensor 500 can be transmitted to the cores 320 of the digital yarn 300. The reason for this is because of the fact that in the case where the second fabric sensor 500 is coupled to the first fabric sensor 200, the second fabric sensor 500 is disposed closest to the body of the wearer who wears the sheet-type member 100. Preferably, portions of the digital yarn 300 in which the peeled portions are formed include a portion (an upper portion in the drawings) that faces the second fabric sensor 500.

To prevent abrasion of the sewing yarn 400, a short circuit of the digital yarn 300, or contamination or poor connection of the peeled portions during washing or due to long-term use of the sheet-type member, the second fabric sensor 500 is preferably closely coupled to the first fabric sensor 200 with the digital yarn 300 interposed therebetween.

In an embodiment, the second fabric sensor 500 may be coupled to the first fabric sensor 200 by fusing or sewing the perimeter of the second fabric sensor 500 to the first fabric sensor 200. Preferably, adhesive is applied on one surface of the second fabric sensor 500, and the second fabric sensor 500 is adhered to the first fabric sensor 200 such that the second fabric sensor 500 is brought into as close contact with the first fabric sensor 200 as possible.

More preferably, a conductive adhesive may be used to bond the second fabric sensor 500 on the first fabric sensor 200. As shown in the present embodiment, in the case where the second fabric sensor 200 is coupled on the first fabric sensor 200 with the digital yarn 300 interposed therebetween, the digital yarn 300 can be reliably electrically connected to the second fabric sensor 500 even when only an upper portion of the digital yarn 300 (that faces the second fabric sensor 500) is peeled. Therefore, there is an advantage in that the peeling operation can be simplified.

Figure 2:
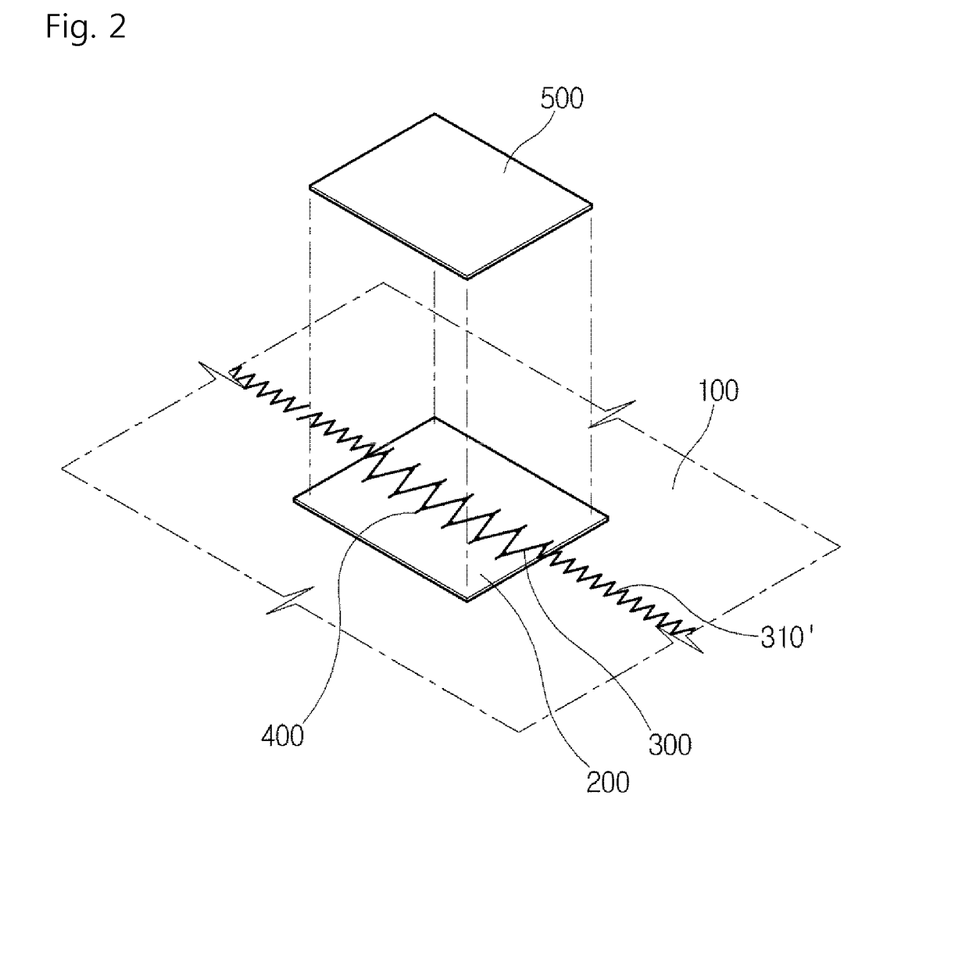
FIG. 2 is a perspective view illustrating a structure for connecting a fabric sensor and a digital yarn according to another embodiment of the present invention.

FIG. 2 is a perspective view illustrating a structure for connecting a fabric sensor and a digital yarn according to another embodiment of the present invention.

The form in which the digital yarn 300 is sewn to the sheet-type member 100 can be changed into various forms. FIG. 1 illustrates an example in which a sewing line 310 formed by sewing the digital yarn 300 to the sheet-type member 100 is linear. In another embodiment of the present invention, as shown in FIG. 2, a sewing line 310' may be formed in a zigzag manner so that the digital yarn 300 can be more firmly coupled to the sheet-type member 100. Alternatively, the digital yarn 300 may be coupled to the sheet-type member 100 by an embroidering method. In addition, the sewing line formed by the digital yarn 300 may be formed in a predetermined pattern.

FIG. 3 is a sectional view of the digital yarn according to an embodiment of the present invention.

As shown in FIG. 3, the digital yarn 300 includes a plurality of cores 320 which are disposed on a diametrical center of the digital yarn, and a sheath 330 which is formed around the cores 320 to enclose the cores 320. Spaces 340 are formed between the cores 320 and the sheath 330 because the inner circumferential surface of the sheath 330 cannot enter areas between the cores 320.

The cores 320 are made of metal which has a low electrical resistance and a high elastic restoring force against repeated bending. For example, each core 320 may be formed of a metal filament that is made of copper, a copper alloy, silver, a silver alloy, gold, a gold alloy, brass, etc. having a comparatively high conductivity. The diameter of each core 320 ranges from 50 µm to 200 µm. Furthermore, although an example including seven cores 320 is illustrated in FIG. 3, the present invention is not limited to this.

The sheath 330 is formed to enclose the cores 320. The sheath 330 functions not only to prevent electromagnetic waves generated by the cores 320 from affecting the body of the wearer but also to block external noise electromagnetic waves from reaching the cores 320. For this, the sheath 330 is preferably made of any one of ethylene tetrafluoroethylene (FTFE), fluorinated ethylenepropylene (FEP), polytetrafluoroethylene (PTFE), polyvinylidene fluoride (PVDF), perfluoroalkoxy (PFA), and equivalents, but the present invention is not limited to this.

Figure 4:
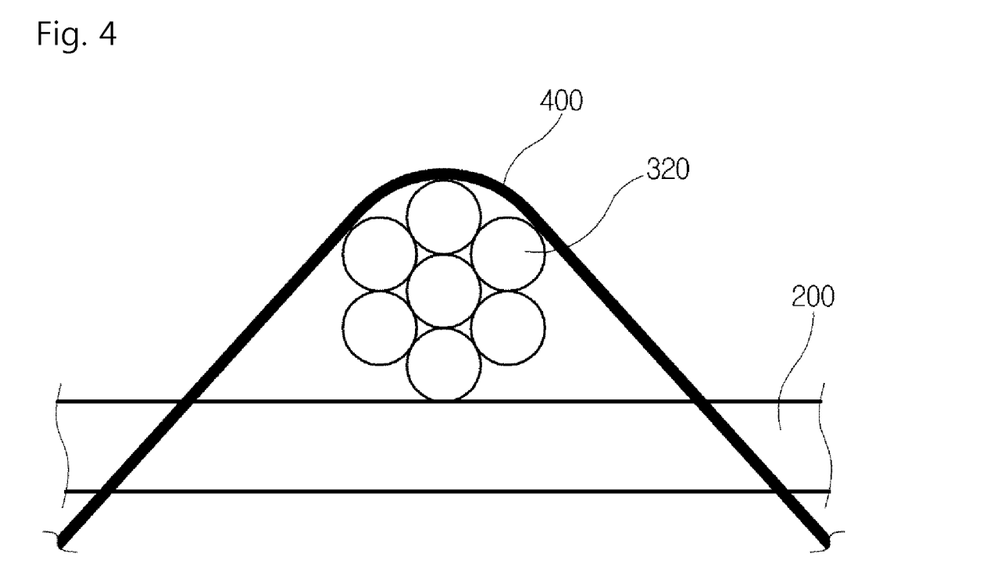
FIG. 4 is a schematic sectional view illustrating a structure of sewing a digital yarn to a first fabric sensor with a sewing yarn crossing over the digital yarn according to an embodiment of the present invention.

FIG. 4 is a schematic sectional view illustrating a structure of sewing the digital yarn to the first fabric sensor with a sewing yarn crossing over the digital yarn according to an embodiment of the present invention.

As shown in FIG. 4, the digital yarn 300 is sewn to the first fabric sensor 200 by the sewing yarn 400 wrapping around the digital yarn 300. FIG. 4 illustrates an example in which the entirety of the cores 320 is exposed to the outside by peeling the circumferential entirety of a portion of the sheath of the digital yarn 300. In this case, some of the cores 320 that are disposed in a lower portion thereof can be electrically connected to the first fabric sensor 200. Some of the cores 320 that are disposed in an upper portion thereof can be electrically connected to the above-mentioned second fabric sensor 500.

In another example, only a lower portion of the sheath of the digital yarn 300 illustrated in FIG. 3 may be peeled. In this case, some of the cores 320 that are disposed in a lower portion thereof are exposed to the outside through the peeled portion and electrically connected to the first fabric sensor 200.

In yet another example, only an upper portion of the sheath of the digital yarn 300 illustrated in FIG. 3 may be peeled. In this case, some of the cores 320 that are disposed in an upper portion thereof are exposed to the outside through the peeled portion and electrically connected to the second fabric sensor 500.

Preferably, a plurality of peeled portions are formed at positions spaced apart from each other with respect to the longitudinal direction of the digital yarn 300.

The sewing yarn 400 can couple the digital yarn 300 to the first fabric sensor 200 in various manners, e.g., backstitching. The digital yarn 300 is sewn to the first fabric sensor 200 such that the outer circumferential surface of the digital yarn 300 is compressed toward the first fabric sensor 200. That is, the sewing yarn 400 sewn to the first fabric sensor 200 forms a hook shape to fasten a portion of the digital yarn 300 to the first fabric sensor 200. A biological signal sensed by the first or second fabric sensor 200 or 500 is transmitted to the digital yarn 300 through the peeled portion and transferred to the above-mentioned device along the digital yarn 300.

Figure 5:
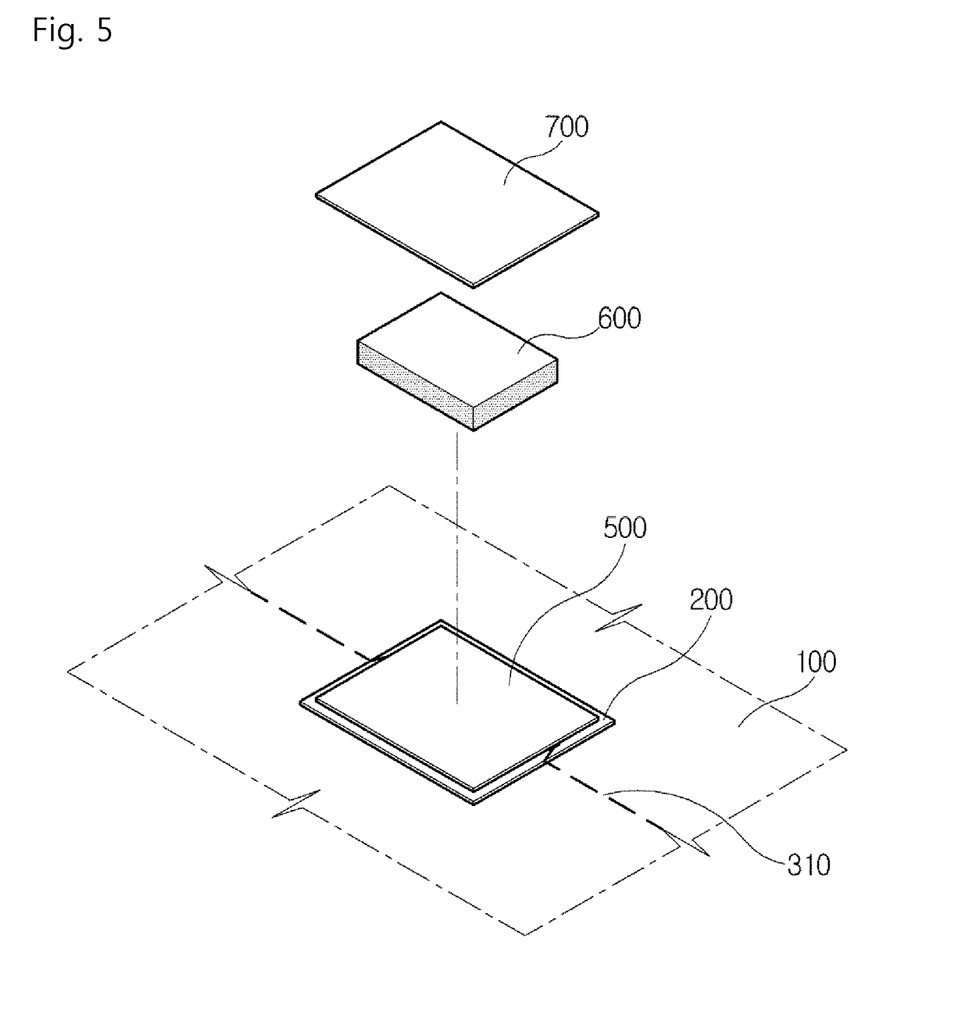
FIG. 5 is an exploded perspective view illustrating a structure for connecting a fabric sensor and a digital yarn according to yet another embodiment of the present invention.
Figure 6:
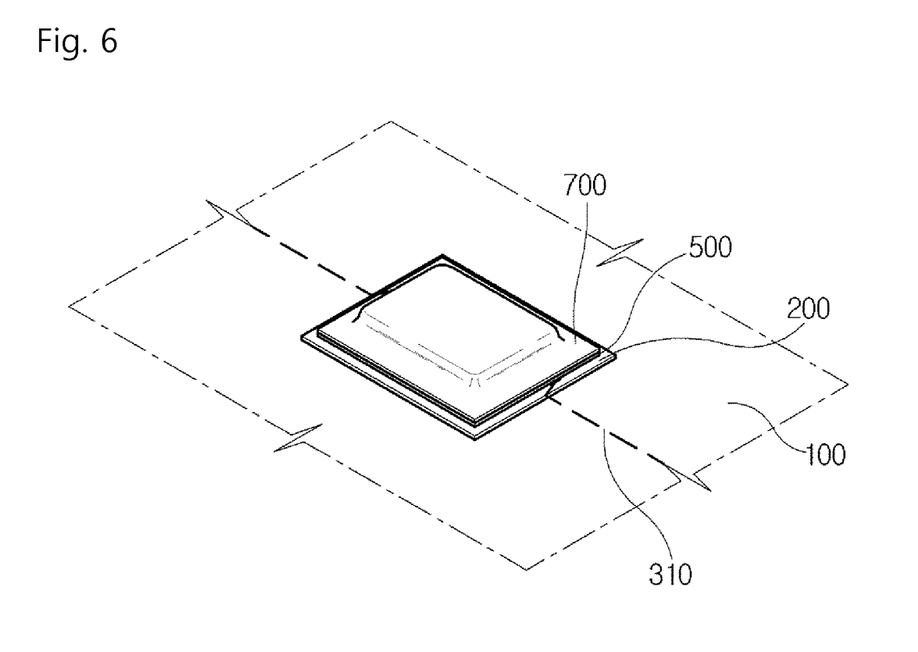
FIG. 6 is an assembled perspective view of FIG. 5.

FIG. 5 is an exploded perspective view illustrating a structure for connecting a fabric sensor and a digital yarn according to yet another embodiment of the present invention. FIG. 6 is an assembled perspective view of FIG. 5.

Depending on the kind of fabric sensor, there may be the need for the fabric sensor to come into close contact with the body of the wearer so as to increase the reliability of measured values. For this, it is preferable that the sheet-type member 100 formed in a form of clothes or an elastic band be made of material having a relatively high elasticity or be designed in a shape in which the sheet-type member 100 can be brought into close contact with the body of the wearer when it is worn on the body.

However, the elasticity of the sheet-type member 100 may be reduced by abrasion due to use for a long period of time or by damage caused when it is washed. Furthermore, if the wearer has purchased a product having the sheet-type member 100 with a larger size or the body of the wearer has been changed, for example, by reducing the weight of the body, the degree to which the fabric sensor comes into close contact with the body of the wearer may be reduced. As a result, the reliability of measured values may deteriorate.

In consideration of this, in the present embodiment, an elastic member 600 made of material such as urethane foam is placed on the second fabric sensor 500. A third fabric sensor 700 is coupled on the second fabric sensor 500 with the elastic member 600 interposed therebetween. In this case, when the wearer wears the sheet-type member 100, the third fabric sensor 700 can be brought into close contact with the body of the wearer by the elasticity of the elastic member 600. Biometric data measured by the third fabric sensor 700 is transmitted to the digital yarn 300 through the first fabric sensor 200 or the second fabric sensor 500.

Preferably, the third fabric sensor 700 is coupled to the second fabric sensor 500 by sewing the perimeter of the third fabric sensor 700. Of course, the perimeter of the third fabric sensor 700 may be fused to the first fabric sensor 200 or the second fabric sensor 500. Alternatively, the perimeter of the third fabric sensor 700 may be adhered to the first fabric sensor 200 or the second fabric sensor 500 by conductive adhesive. Here, the elastic member 600 is preferably adhered to the second fabric sensor 500 so as to prevent the elastic member 600 from moving.

Figure 7:
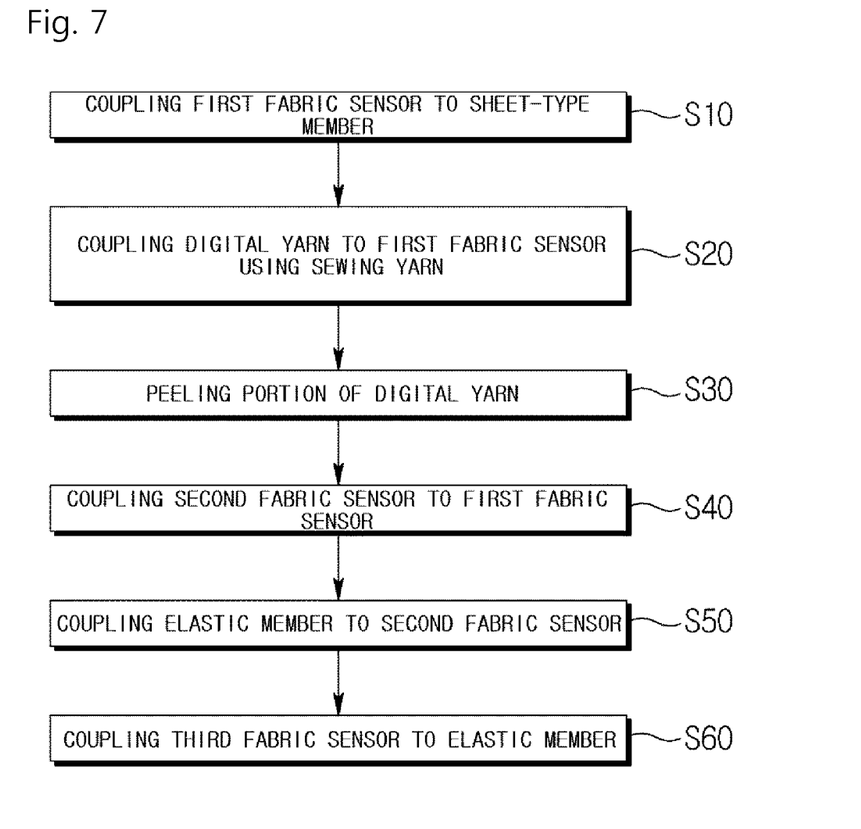
FIG. 7 is a flowchart showing a method for connecting a fabric sensor and a digital yarn according to an embodiment of the present invention.

FIG. 7 is a flowchart showing a method for connecting a fabric sensor and a digital yarn according to an embodiment of the present invention. Hereinafter, the method for connecting the fabric sensor and the digital yarn according to the embodiment of the present invention will be described with reference to FIG. 7.

Coupling of the First Fabric Sensor to the Sheet-Type Member (at S10)

The first fabric sensor 200 is coupled to the sheet-type member 100 that forms clothes or an elastic band. In the present embodiment, the first fabric sensor 200 may be adhered to the inner surface of the sheet-type member 100 by adhesive. Alternatively, the perimeter of the first fabric sensor 200 may be sewn to the sheet-type member 100. As a further alternative, when the sheet-type member 100 such as the clothes or elastic band is woven, the first fabric sensor 200 may be integrally woven with the sheet-type member 100.

Coupling the Digital Yarn to the First Fabric Sensor Using a Sewing Yarn (at S20)

The connector to which a display or a wireless transmitter is connected may be provided on a portion (for example, a front pocket of a lower portion) of the sheet-type member 100. The digital yarn 300 connected to the connector extends in such a way that the digital yarn 300 is sewn to the sheet-type member 100 and is connected to the first fabric sensor 100.

In more detail, the digital yarn 300 is coupled to the first fabric sensor 200 by the sewing yarn 400 in a zigzag manner. In this embodiment, the digital yarn 300 is disposed on the first fabric sensor 200 in a zigzag form. The sewing yarn 400 wraps over an upper portion of the outer circumferential surface of the digital yarn 300 at each vertex of the zigzag-formed digital yarn 300 and is sewn to the first fabric sensor 200. That is, the sewing yarn 400 is sewn in a hook form to the first fabric sensor 200 at each vertex of the zigzag-formed digital yarn 300, thus compressing the digital yarn 300 onto the first fabric sensor 200 so that the digital yarn 300 can be reliably fastened to the first fabric sensor 200. The operation of extending the digital yarn 300 in a zigzag form and sewing the vertices of the zigzag-formed digital yarn 300 to the first fabric sensor 200 with the sewing yarn 400 may be automatically conducted by a sewing machine.

Peeling a Portion of the Digital Yarn (at S30)

A portion of the digital yarn 300 is peeled to form a peeled portion. Forming the peeled portion is to electrically connect the digital yarn 300 to the first fabric sensor 200 or the second fabric sensor 500, which will be described later herein. Preferably, a plurality of peeled portions are formed at positions spaced apart from each other with respect to the longitudinal direction of the digital yarn 300. The peeled portion may be formed by heating a portion of the sheath 330 of the digital yarn 300 or by a laser marking apparatus. Preferably, to prevent thermal deformation of the digital yarn 300, a portion of the sheath 330 is mechanically peeled using a separate peeling apparatus such as a cutter.

Coupling the Second Fabric Sensor to the First Fabric Sensor (at S40)

The second fabric sensor 500 is coupled on the first fabric sensor 200 and thus covers the peeled portion of the digital yarn 300 so that the peeled portion can be prevented from being exposed to the outside. The coupling of the second fabric sensor 500 to the first fabric sensor 200 may be conducted by fusing or sewing and, more preferably, by applying conductive adhesive to one surface of the second fabric sensor 500 and adhering the second fabric sensor 500 to the first fabric sensor 200.

The digital yarn 300 having the peeled portion is interposed between the first fabric sensor 200 and the second fabric sensor 500. As the second fabric sensor 500 is brought into close contact with and fixed to the first fabric sensor 200, the peeled portion of the digital yarn 300 is brought into close contact with and fixed to the first fabric sensor 200 and the second fabric sensor 500.

At the preceding step (S30), if the peeled portion is formed on an upper portion of the digital yarn 300, the cores 320 of the digital yarn 300 are electrically connected to the second fabric sensor 500 when the second fabric sensor 500 is coupled to the first fabric sensor 200. Therefore, biometric data that is sensed by the second fabric sensor 500 and converted into an electrical signal can be transmitted through the digital yarn 300.

Coupling the Elastic Member to the Second Fabric Sensor (at S50)

Connection of the digital yarn with the fabric sensor according to the embodiment of the present invention is embodied, at the preceding step (S40), that is, by coupling the second fabric sensor 500 to the first fabric sensor 200 such that the digital yarn 300 is covered with the second fabric sensor 500.

According to another embodiment of the present invention, the elastic member 600 may be coupled to the second fabric sensor 500 so that the fabric sensor can be reliably brought into close contact with the body of the wearer in order to enhance the reliability of measured values. The elastic member 600 is made of material such as urethane foam having a relatively high elasticity and is preferably adhered to the second fabric sensor 500.

Coupling the Third Fabric Sensor to the Elastic Member (at S60)

The third fabric sensor 700 is coupled on the elastic member 600. The third fabric sensor 700 is electrically connected to the first fabric sensor 200 or the second fabric sensor 500. Preferably, third fabric sensor 700 is reliably fixed to the second fabric sensor 500 by sewing along the perimeter of the third fabric sensor 700.

In this case, when the wearer wears the sheet-type member 100, the third fabric sensor 700 is brought into close contact with the body of the wearer by the elasticity of the elastic member 600. Biometric data sensed from the body of the wearer by the third fabric sensor 700 is transmitted to the digital yarn 300 through the first fabric sensor 200 or the second fabric sensor 500 that is electrically connected to the third fabric sensor 700.

The biometric data transmitted to the connector through the digital yarn 300 can be displayed by the display connected to the connector. In the case where the wireless transmitter is connected to the connector, the biometric data is transmitted to a data processing unit such as a PC or cellular phone through the wireless transmitter and is displayed by a display of the data processing unit.

A plurality of fabric sensors which senses different kinds of biometric data may be provided on the sheet-type member 100. The plurality of fabric sensors may be connected to the connector through a plurality of digital yarns 300. In other words, according to an embodiment of the present invention, different kinds of biometric data can be measured and checked at the same time by the multiple fabric sensors.

Although some detailed embodiments of the present invention have been described above, the embodiments have been provided to describe the present invention in detail, and the present invention is limited to the embodiments. It is evident to those skilled in the art that the present invention may be modified or improved within the technical spirit of the present invention.

Such a simple modification or change of the present invention falls within the scope of the present invention, and a detailed scope of the present invention will become evident by the appended claims.

The invention claimed is:

1. A structure for connecting a fabric sensor and a digital yarn, comprising:
   a sheet-type member configured to be worn on a body of a wearer;
   a first fabric sensor provided on the sheet-type member for sensing a biological signal;
   a digital yarn comprising at least one core and a sheath covering the core provided on the first fabric sensor, with a portion of the sheath peeled from the core to form a peeled portion, the peeled portion being electrically connected to the first fabric sensor;
   a sewing yarn coupling a portion of the digital yarn to the first fabric sensor by sewing; and
   a second fabric sensor coupled to the first fabric sensor and covering an upper portion of the peeled portion.

2. The structure of claim 1, wherein the peeled portion is formed on an upper portion of the digital yarn, and the second fabric sensor is electrically connected to the peeled portion.

3. The structure of claim 1, wherein the second fabric sensor is adhered to the first fabric sensor by a conductive adhesive.

4. The structure of claim 1, wherein the second fabric sensor is sewn to the first fabric sensor along a perimeter of the second fabric sensor.

5. The structure of claim 1, wherein a third fabric sensor is coupled to the second fabric sensor, and an elastic member is interposed between the second fabric sensor and the third fabric sensor.

6. The structure of claim 1, wherein the digital yarn is disposed on the first fabric sensor in a zigzag form, and the sewing yarn is sewn to a vertex of the zigzag-formed digital yarn.

7. A method for connecting a fabric sensor and a digital yarn, comprising:
   (a) coupling a first fabric sensor to a sheet-type member configured to be worn on a body of a wearer;
   (b) coupling a digital yarn to the first fabric sensor; and
   (c) peeling a portion of a sheath of the digital yarn and electrically connecting the peeled portion of the digital yarn to the first fabric sensor,
   wherein (b) coupling comprises sewing the digital yarn to the first fabric sensor using a sewing yarn crossing over a portion of the digital yarn,
   the method further comprising:
   (d) coupling a second fabric sensor to the first fabric sensor and covering an upper portion of the peeled portion of the digital yarn with the second fabric sensor.

8. The method of claim 7, wherein (b) coupling comprises disposing the digital yarn on the first fabric sensor in a zigzag form, and sewing the sewing yarn to a vertex of the zigzag-formed digital yarn.

9. The method of claim 7, wherein the peeled portion is formed by peeling an upper portion of the sheath of the digital yarn, and the second fabric sensor is electrically connected to the peeled portion.

10. The method of claim 7, wherein (d) coupling comprises adhering the second fabric sensor to the first fabric sensor using a conductive adhesive.

11. The method of claim 7, wherein (d) coupling comprises sewing the second fabric sensor to the first fabric sensor along a perimeter of the second fabric sensor.

12. The method of claim 7, further comprising
(e) coupling a third fabric sensor to the second fabric sensor with an elastic member interposed between the second fabric sensor and the third fabric sensor.

* * * * *